(12) United States Patent
Somekawa et al.

(10) Patent No.: US 9,629,386 B2
(45) Date of Patent: Apr. 25, 2017

(54) NUTRITION COMPOSITION

(75) Inventors: Shinji Somekawa, Shizuoka (JP);
Tomoyuki Mine, Shizuoka (JP); Naoki Hayashi, Shizuoka (JP)

(73) Assignee: AJINOMOTO CO., INC., Tokyo (JP)

(*) Notice: Subject to any disclaimer, the term of this patent is extended or adjusted under 35 U.S.C. 154(b) by 0 days.

(21) Appl. No.: 13/152,574

(22) Filed: Jun. 3, 2011

(65) Prior Publication Data

US 2011/0288012 A1    Nov. 24, 2011

Related U.S. Application Data

(63) Continuation of application No. PCT/JP2009/070432, filed on Dec. 4, 2009.

(30) Foreign Application Priority Data

Dec. 5, 2008 (JP) .................................. 2008-310955

(51) Int. Cl.
| | | |
|---|---|---|
| A23L 2/52 | (2006.01) | |
| A23L 2/66 | (2006.01) | |
| A61K 31/198 | (2006.01) | |
| A61K 31/202 | (2006.01) | |
| A61K 31/4172 | (2006.01) | |
| A61K 45/06 | (2006.01) | |
| A23L 33/12 | (2016.01) | |
| A23L 33/15 | (2016.01) | |
| A23L 33/175 | (2016.01) | |
| A23L 33/18 | (2016.01) | |
| A23L 33/185 | (2016.01) | |

(52) U.S. Cl.
CPC ........ *A23L 2/52* (2013.01); *A23L 2/66* (2013.01); *A23L 33/12* (2016.08); *A23L 33/15* (2016.08); *A23L 33/175* (2016.08); *A23L 33/18* (2016.08); *A23L 33/185* (2016.08); *A61K 31/198* (2013.01); *A61K 31/202* (2013.01); *A61K 31/4172* (2013.01); *A61K 45/06* (2013.01); *A23V 2002/00* (2013.01)

(58) Field of Classification Search
CPC .......................... A23L 1/3008; A23L 1/3051
USPC ............................................ 426/5, 560, 656
See application file for complete search history.

(56) References Cited

U.S. PATENT DOCUMENTS

| | | | |
|---|---|---|---|
| 5,728,678 A | 3/1998 | Trimbo et al. | |
| 5,780,451 A * | 7/1998 | DeMichele et al. | 514/54 |
| 6,077,828 A | 6/2000 | Abbruzzese et al. | |
| 2004/0067224 A1 | 4/2004 | Ernest | |
| 2004/0087490 A1 | 5/2004 | Troup et al. | |
| 2005/0070498 A1 | 3/2005 | Ernest | |
| 2006/0159746 A1 | 7/2006 | Troup et al. | |
| 2006/0166935 A1 | 7/2006 | Bryhn | |
| 2007/0166411 A1 * | 7/2007 | Anthony et al. | 424/750 |
| 2009/0238893 A1 | 9/2009 | Langford et al. | |
| 2011/0150824 A1 | 6/2011 | Faber et al. | |
| 2011/0152184 A1 | 6/2011 | Van Norren et al. | |
| 2015/0004130 A1 | 1/2015 | Faber et al. | |

FOREIGN PATENT DOCUMENTS

| | | |
|---|---|---|
| EP | 0 689 835 | 1/1996 |
| EP | 0 747 395 | 12/1996 |
| JP | 08-073351 | 3/1996 |
| JP | 11-508282 | 7/1999 |
| JP | 2001-288107 | 10/2001 |
| JP | 2006-503105 | 1/2006 |
| JP | 2006-520335 | 9/2006 |
| JP | 2008-528475 | 7/2008 |
| JP | 2008-247896 | 10/2008 |
| WO | WO 02/069964 | 9/2002 |
| WO | 2005/094813 | 10/2005 |
| WO | WO 2007/146313 A1 | 12/2007 |
| WO | WO 2008/001086 | 1/2008 |
| WO | WO 2009/157759 | 12/2009 |
| WO | WO 2010/002242 | 1/2010 |

OTHER PUBLICATIONS

Stenvinkel et al., "Strong association between malnutrition, inflammation, and atherosclerosis in chronic renal failure"—Kidney International, vol. 55 (1999), pp. 1899-1911.*
International Search Report issued Jan. 12, 2010 in PCT/JP09/070432.
Saifullah, A. et al, Nephrol Dial Transplant (2007), vol. 22, No. 12, p. 3561-7.
Jolly, C.A. et al, J. Nutr. (2001), vol. 131, No. 10, p. 2753-60.
Lefkowith, J.B. et al. Proc. Soc. Exp. Boil. Med. (1996), vol. 213, No. 1, p. 13-23.
Supplementary European Search Report issued Feb. 17, 2015, in European Application No. 09830480 filed Dec. 4, 2009.
Deutz et al., "Protein intake and exercise for optimal muscle function with aging: Recommendations from the ESPEN Expert Group", Clinical Nutrition, vol. 33, 2014, pp. 929-936.

* cited by examiner

*Primary Examiner* — Elizabeth Gwartney
(74) *Attorney, Agent, or Firm* — Oblon, McClelland, Maier & Neustadt, L.L.P.

(57) ABSTRACT

The present invention can provide a nutrition composition useful for patients with renal diseases, which has an effective prophylactic or improving effect for various symptoms of malnutrition, inflammation, arteriosclerosis, abnormal lipid metabolism and oxidative stress, associated with renal diseases, or for diabetic nephropathy.
The nutrition composition of the present invention m contains one or more kinds of free amino acids selected from the group consisting of valine, leucine, isoleucine and histidine, and a lipid comprising ω-3 fatty acid and ω-6 fatty acid at a weight ratio (ω-6 fatty acid to ω-3 fatty acid) of 0.5-5.5. In addition, the composition further contains a soybean protein or a hydrolysate thereof together with the aforementioned lipid or instead of the aforementioned lipid.

21 Claims, No Drawings

NUTRITION COMPOSITION

CROSS REFERENCES TO RELATED APPLICATIONS

This application is a Continuation Application of International Patent Application No. PCT/JP2009/070432, filed on Dec. 4, 2009, and claims priority to Japanese Patent Application No. 2008/310955, filed on Dec. 5, 2008.

TECHNICAL FIELD

The present invention relates to a nutrition composition useful for patients with a renal disease. More specifically, it relates to a nutrition composition comprising a particular fatty acid and an amino acid, or further comprising a soybean protein, and useful for the prevention or improvement of malnutrition, inflammation or arteriosclerosis and the like associated with renal diseases.

BACKGROUND ART

Renal diseases include inflammatory renal diseases such as nephritic syndrome, nephrotic syndrome and the like, angiopathic diseases such as atheroembolic renal disease, renal vein thrombosis and the like, diabetic nephropathy caused by diabetes and the like. In patients with such renal diseases, nutritional deficiency, i.e., malnutrition, is often found, and malnutrition is an important factor that influences the prognosis of patients with renal diseases. In addition, when kidney function decreases due to the aforementioned diseases, shortage of blood flow into the kidney due to hemorrhage, cardiac failure and the like, urinary tract obstruction due to prostatic hyperplasia and the like, kidney damage and the like, acute or chronic renal failure is developed, sometimes requiring artificial dialysis to sustain life. Among the dialysis-introduced patients, a condition called MIA syndrome wherein malnutrition, chronic inflammation and arteriosclerosis are related to each other to exert an adverse influence has been a problem. Furthermore, when the blood C-reactive protein (CRP) concentration, which is one of the indices of inflammation, is not less than 0.2 mg/dL on dialysis introduction, the risk of death is reported to increase when the value is higher (non-patent document 1). Currently, however, an appropriate treatment method for these patients has not been established, and the patients are dealt with by performance of an optimal dialysis for each patient, determination of an optimal amount of dialysis, and removal of endotoxin in dialysates.

The above-mentioned malnutrition of patients with renal diseases is preferably dealt with by improvement with nutrition supplements. However, when inflammation persists, normal nutrition supplementation is not expected to provide a sufficient improvement effect, since various biological reactions occur such as reduction in appetite, degradation of body protein, increase of protein catabolism, decrease of protein anabolism, hypermetabolism due to cytokine and the like.

As a medical preparation for patients with renal diseases, a preparation containing reduced amounts of protein, phosphorus, potassium, sodium and water as compared to general-purpose liquid foods has been used heretofore. As an amino acid preparation for renal failure, moreover, "Amiyu® granule", "Neoamiyu®" and the like containing a higher amount of essential amino acid (manufactured by Ajinomoto Pharma Co., Inc.) are commercially available. However, the products do not contain lipid, which is an important nutrient for energy supplementation and suppression of inflammation, and these medical preparations have not shown a clear improvement of inflammation.

On the other hand, a report has documented that, in a pilot test by dialysis patients, the blood CRP concentration decreased by administration of a fish oil capsule containing 427 mg of eicosapentaenoic acid and 244 mg of docosahexaenoic acid for 12 weeks (non-patent document 2). However, since the aforementioned fish oil capsule does not contain protein, it does not improve malnutrition. It has also been reported that administration of 1.2 g of ω-3 fatty acid to 11 dialysis patients for 12 weeks did not decrease CRP and did not improve nutrition condition (non-patent document 3). Furthermore, since ω-3 fatty acid such as eicosapentaenoic acid and the like has a problematic taste, it needs to be considered that addition in a high concentration is poor compliance, and may cause a bleeding tendency due to it's platelet aggregation suppressive action. With ω-3 fatty acid alone, therefore, inflammation suppressive and malnutrition improving effects in dialysis patients cannot be expected, which suggests the need for use in combination with other nutrients.

When a nutrition composition with a ratio of ω-6 fatty acid/ω-3 fatty acid in fatty acid of 1.6 was administered for 4 weeks to dialysis patients associated by malnutrition and inflammation, a significant decrease in CRP or increase in body weight was not found (non-patent document 4). The content of protein in the composition described in this document is as high as 3.8 g/100 kcal, which prevents easy application thereof to patients under restriction of protein intake. Furthermore, since the aforementioned composition does not contain free amino acid, and shows low selenium and zinc contents, the importance thereof is also suggested.

On the contrary, patent document 1 discloses a nutrition composition containing protein, fat, carbohydrate, vitamin, mineral and L-arginine. However, when nitric oxide (NO) is produced in excess by L-arginine, hypotension may be induced. Thus, a long-term administration of this nutrition composition requires attention. Moreover, patent document 2 discloses a composition for patients with cachexia and/or anorexia, which contains a mixed oil with a weight ratio of ω-6 fatty acid to ω-3 fatty acid of 0.1-3.0, amino acid containing branched chain amino acid, and antioxidant such as β-carotene, vitamin C, vitamin E, selenium and the like. Different from healthy individual, however, patients with renal diseases are feared to develop side effects due to the administration of large amounts of vitamin A and vitamin C. These contents of the composition are not suitable for patients with renal diseases.

For renal diseases showing malnutrition such as hypoproteinemia and the like, a nutrition composition with an attention to protein supplementation is desired. Non-patent document 5 discloses that, by ingestion of a soybean protein, glomerular filtration rate of the kidney, renal plasma flow and fractional clearance of albumin decrease, and renal vasodilator action, which is observed with ingestion of animal-derived protein, is eliminated, thus suggesting a less load applied by soybean protein on the kidney.

The present Applicant already found usefulness of branched chain amino acid, and disclosed a life prognosis-improving agent for patients with renal diseases, which contains branched chain amino acid (patent document 3). With regard to histidine, which has been considered an essential amino acid in renal diseases from long ago and is known to show an antioxidant action, the plasma histidine concentration of patients with chronic renal diseases has been shown to significantly decrease (non-patent document 6). However, they do not consider lipid, and branched chain amino acid or histidine, and a lipid containing ω-3 fatty acid and ω-6 fatty acid at a particular weight ratio, and further, a soybean protein have not been used in combination.

As one of the causes of arteriosclerosis, which is one pathology of MIA syndromes, low-density lipoprotein (LDL) peroxide produced by denaturation of LDL cholesterol due to an oxidative stress is known, and an antioxidant substance is important for the improvement of MIA syndromes. Therefore, patients with renal diseases who show MIA syndrome, and abnormal lipid metabolism such as high LDL-cholesterolemia and the like desire a nutrition composition with consideration of the above-mentioned substance, factors and the like. However, such composition has not been known to date.

DOCUMENT LIST

Patent Documents patent document 1: National Publication of International Patent Application No. 2002-514575
patent document 2: National Publication of International Patent Application No. H11-508282
patent document 3: WO2005/094813

Non-Patent Documents non-patent document 1: An overview of regular dialysis treatment in Japan, as of Dec. 31, 2007, The Japanese Society for Dialysis Therapy, published on Jun. 19, 2008, pages 51-73
non-patent document 2: Nephrol. Dial. Transplant. 22 (12) 3561-3567 (2007)
non-patent document 3: J. Renal Nutrition 15 (2) 253-256 (2005)
non-patent document 4: J. Renal Nutrition 15 (3) 318-331 (2005)
non-patent document 5: Kidney Int. 38 136-144 (1990)
non-patent document 6: Am. J. Clin. Nutr. 87 1860-1866 (2008)

SUMMARY OF THE INVENTION

Problems to be Solved by the Invention

Therefore, the present invention aims to provide a nutrition composition having a preventive or improving effect useful for malnutrition, inflammation, arteriosclerosis, abnormal lipid metabolism and the like associated with renal diseases, which is particularly useful for patients with renal diseases.

Means of Solving the Problems

As the result of various studies in an attempt to solve the above-mentioned problems, the present inventors have found that symptoms of malnutrition, inflammation, arteriosclerosis, abnormal lipid metabolism and the like can be effectively improved, or expression of these symptoms can be effectively prevented by containing one or more kinds of free amino acids selected from the group consisting of valine, leucine, isoleucine and histidine, and a lipid containing ω-3 fatty acid and ω-6 fatty acid at a particular weight ratio, or a soybean protein or a hydrolysate thereof together with the aforementioned lipid, or instead of the aforementioned lipid, which resulted in the completion of the present invention.

Accordingly, the present invention relates to the following [1] to [42].

[1] A nutrition composition comprising one or more kinds of free amino acids selected from the group consisting of valine, leucine, isoleucine and histidine, and a lipid comprising ω-3 fatty acid and ω-6 fatty acid at a weight ratio (ω-6 fatty acid to ω-3 fatty acid) of 0.5-5.5.

[2] The nutrition composition of the above-mentioned [1], further comprising a soybean protein or a hydrolysate thereof.

[3] A nutrition composition comprising one or more kinds of free amino acids selected from the group consisting of valine, leucine, isoleucine and histidine, and a soybean protein or a hydrolysate thereof.

[4] The nutrition composition of any of the above-mentioned [1] to [3], wherein the one or more kinds of free amino acids selected from the group consisting of valine, leucine, isoleucine and histidine is(are) contained in a proportion of 0.1 g-10 g per 100 kcal of the composition.

[5] The nutrition composition of any of the above-mentioned [2] to [4], wherein the total amount of the protein and peptide (excluding amino acids) per 100 kcal of the composition is not more than 3.5 g, and the content of the soybean protein or a hydrolysate thereof in the protein or peptide is 20 wt %-100 wt %.

[6] The nutrition composition of the above-mentioned [1] or [2], wherein the ω-3 fatty acid is one or more kinds of fatty acid selected from the group consisting of α-linolenic acid, eicosapentaenoic acid, docosapentaenoic acid and docosahexaenoic acid.

[7] The nutrition composition of any of the above-mentioned [1], [2] and [6], wherein the ω-6 fatty acid is one or more kinds of fatty acid selected from the group consisting of linoleic acid, γ-linolenic acid, stearidonic acid and arachidonic acid.

[8] The nutrition composition of any of the above-mentioned [1] to [7], wherein the lipid comprises 10 wt %-65 wt % of medium chain fatty acid oil.

[9] The nutrition composition of any of the above-mentioned [1] to [8], comprising 5 mg-150 mg of vitamin C and/or not less than 1 mg of vitamin E, per 100 kcal of the composition.

[10] The nutrition composition of any of the above-mentioned [1] to [9], comprising 2.5 μg-45 μg of selenium and 1 mg-9 mg of zinc, per 100 kcal of the composition.

[11] The nutrition composition of any of the above-mentioned [1] to [10], which is for a patient with a renal disease.

[12] The nutrition composition of any of the above-mentioned [1] to [10], which is for the prevention or improvement of malnutrition associated with renal disease.

[13] The nutrition composition of any of the above-mentioned [1] to [10], which is for the prevention or improvement of inflammation associated with renal disease.

[14] The nutrition composition of any of the above-mentioned [1] to [10], which is for the prevention or improvement of arteriosclerosis associated with renal diseases.

[15] The nutrition composition of any of the above-mentioned [1] to [10], which is for the prevention or improvement of abnormal lipid metabolism associated with renal disease.

[16] The nutrition composition of any of the above-mentioned [1] to [10], which is for the prevention or improvement of oxidative stress associated with renal disease.

[17] The nutrition composition of any of the above-mentioned [1] to [10], which is for the prevention or improvement of diabetic nephropathy.

[18] An agent for the prevention or improvement of one or more symptoms selected from the group consisting of malnutrition, inflammation, arteriosclerosis, abnormal lipid metabolism and oxidative stress, associated with renal diseases, comprising one or more kinds of free amino acids selected from the group consisting of valine, leucine, isoleucine and histidine, and a lipid comprising ω-3 fatty acid and ω-6 fatty acid at a weight ratio (ω-6 fatty acid to ω-3 fatty acid) of 0.5-5.5.

[19] An agent for the prevention or improvement of diabetic nephropathy, comprising one or more kinds of free amino acids selected from the group consisting of valine, leucine, isoleucine and histidine, and a lipid comprising ω-3 fatty acid and ω-6 fatty acid at a weight ratio (ω-6 fatty acid to ω-3 fatty acid) of 0.5-5.5.

[20] The agent for the prevention or improvement of the above-mentioned [18] or [19], further comprising a soybean protein or a hydrolysate thereof.

[21] The agent for the prevention or improvement of the above-mentioned [18] or [19], comprising one or more kinds of free amino acids selected from the group consisting of valine, leucine, isoleucine and histidine in a proportion of 0.1 g-10 g per 100 kcal of the composition.

[22] The agent for the prevention or improvement of the above-mentioned [20], wherein a content of protein or peptide in nitrogen source per 100 kcal of the composition is not more than 3.5 g, and a content of soybean protein or a hydrolysate thereof in the protein or peptide is 20 wt %-100 wt %.

[23] The agent for the prevention or improvement of the above-mentioned [18] or [19], wherein the ω-3 fatty acid is one or more kinds of fatty acids selected from the group consisting of α-linolenic acid, eicosapentaenoic acid, docosapentaenoic acid and docosahexaenoic acid.

[24] The agent for the prevention or improvement of the above-mentioned [18] or [19], wherein the ω-6 fatty acid is one or more kinds of fatty acid selected from the group consisting of linoleic acid, γ-linolenic acid, stearidonic acid and arachidonic acid.

[25] The agent for the prevention or improvement of the above-mentioned [18] or [19], comprising a lipid comprising 10 wt %-65 wt % of medium chain fatty acid oil.

[26] The agent for the prevention or improvement of the above-mentioned [18] or [19], comprising 5 mg-150 mg of vitamin C and/or not less than 1 mg of vitamin E, per 100 kcal of the composition.

[27] The agent for the prevention or improvement of the above-mentioned [18] or [19], comprising 2.5 μg-45 μg of selenium and 1 mg-9 mg of zinc, per 100 kcal of the composition.

[28] An agent for the prevention or improvement of one or more symptoms selected from the group consisting of malnutrition, inflammation, arteriosclerosis, abnormal lipid metabolism and oxidative stress, associated with renal disease, comprising one or more kinds of free amino acids selected from the group consisting of valine, leucine, isoleucine and histidine, and a soybean protein or a hydrolysate thereof.

[29] An agent for the prevention or improvement of diabetic nephropathy, comprising one or more kinds of free amino acids selected from the group consisting of valine, leucine, isoleucine and histidine, and a soybean protein or a hydrolysate thereof.

[30] The agent for the prevention or improvement of the above-mentioned [28] or [29], wherein the one or more kinds of free amino acids selected from the group consisting of valine, leucine, isoleucine and histidine is(are) contained in a proportion of 0.1 g-10 g per 100 kcal of the composition.

[31] The agent for the prevention or improvement of the above-mentioned [28] or [29], wherein the content of the protein or peptide in a nitrogen source per 100 kcal of the composition is not more than 3.5 g, and the content of the soybean protein or a hydrolysate thereof in the protein or peptide is 20 wt %-100 wt %.

[32] The agent for the prevention or improvement of the above-mentioned [28] or [29], comprising a lipid comprising 10 wt %-65 wt % of medium chain fatty acid oil.

[33] The agent for the prevention or improvement of the above-mentioned [28] or [29], comprising 5 mg-150 mg of vitamin C and/or not less than 1 mg of vitamin E, per 100 kcal of the composition.

[34] The agent for the prevention or improvement of the above-mentioned [28] or [29], comprising 2.5 μg-45 μg of selenium and 1 mg-9 mg of zinc, per 100 kcal of the composition.

[35] A method of preventing or improving one or more symptoms selected from the group consisting of malnutrition, inflammation, arteriosclerosis, abnormal lipid metabolism and oxidative stress, associated with renal disease, comprising administering, to a patient with a renal disease, the nutrition composition of the above-mentioned [1] in an amount sufficient to prevent or improve the aforementioned one or more symptoms.

[36] A method of preventing or improving diabetic nephropathy, comprising administering, to a patient with diabetic nephropathy, the nutrition composition of the above-mentioned [1] in an amount sufficient to prevent or improve diabetic nephropathy.

[37] A method of preventing or improving one or more symptoms selected from the group consisting of malnutrition, inflammation, arteriosclerosis, abnormal lipid metabolism and oxidative stress, associated with renal disease, comprising administering, to a patient with a renal disease, the nutrition composition of the above-mentioned [2] in an amount sufficient to prevent or improve the aforementioned one or more symptoms.

[38] A method of preventing or improving diabetic nephropathy, comprising administering, to a patient with diabetic nephropathy, the nutrition composition of the above-mentioned [2] in an amount sufficient to prevent or improve diabetic nephropathy.

[39] A method of preventing or improving one or more symptoms selected from the group consisting of malnutrition, inflammation, arteriosclerosis, abnormal lipid metabolism and oxidative stress, associated with renal disease, comprising administering, to a patient with a renal disease, the nutrition composition of the above-mentioned [3] in an amount sufficient to prevent or improve the aforementioned one or more symptoms.

[40] A method of preventing or improving diabetic nephropathy, comprising administering, to a patient with diabetic nephropathy, the nutrition composition of the above-mentioned [3] in an amount sufficient to prevent or improve diabetic nephropathy.

[41] A commercial package comprising the nutrition composition of any of the above-mentioned [1] to [10], and a written matter stating that the composition can or should be used for preventing or improving one or more symptoms selected from the group consisting of malnutrition, inflammation, arteriosclerosis, abnormal lipid metabolism and oxidative stress, associated with renal disease.

[42] A commercial package comprising the nutrition composition of any of the above-mentioned [1] to [10], and a written matter stating that the composition can or should be used for preventing or improving diabetic nephropathy.

Effect of the Invention

The nutrition composition of the present invention is useful for patients with renal diseases, can effectively prevent or improve malnutrition, inflammation, arteriosclerosis, abnormal lipid metabolism, oxidative stress and the like associated with renal diseases, and is useful for the prevention or improvement of diabetic nephropathy. Furthermore, the nutrition composition of the present invention is highly safe, and can be continuously used as a food for nutrition supplementation for patients with a renal disease and decreased kidney function.

DESCRIPTION OF EMBODIMENTS

The nutrition composition of the present invention comprises one or more kinds of free amino acids selected from the group consisting of valine, leucine, isoleucine and histidine, and a lipid containing ω-3 fatty acid and ω-6 fatty acid such that the weight ratio of ω-6 fatty acid to ω-3 fatty acid is 0.5-5.5. In addition, the composition further comprises a soybean protein or a hydrolysate thereof together with or instead of the above-mentioned lipid.

Valine, leucine and isoleucine to be used in the nutrition composition of the present invention are amino acids having a branched chain, and take an important role in energy source during exercise, maintenance and increase of skeletal muscle, gluconeogenesis and the like. Particularly, leucine and isoleucine are each known to show a suppressive action on postprandial elevation of blood glucose levels. In addition, histidine is one kind of basic amino acid and is involved in the enzyme active center and proton transfer in a protein molecule. It becomes a binding site to a metal in a protein, or takes an important role in the maintenance of a higher-order structure thereof via a hydrogen bond or an ion bond. In the present invention, one or more kinds are selected therefrom and used. In addition, these amino acids are used in a free form in the present invention.

For the object of the present invention, any of an L form, a D form and a DL form can be used as valine, leucine, isoleucine or histidine, and an L form is used most preferably. In addition, as the aforementioned amino acid, any of the amino acids obtained by extraction from animals and plants etc. containing them, and purification thereof, and the amino acids obtained by a chemical synthesis method, a fermentation method or a gene recombination method may be used, and a commercially available product can also be purchased from Sigma-Aldrich Corp. and the like.

In the nutrition composition of the present invention, these amino acids have been found to be more effective when contained in not less than about 0.1 g per 100 kcal, and an increased amount thereof can be used when a stronger effect is expected. In consideration of degradation of the taste, the content thereof per 100 kcal of the composition is preferably 0.1 g-10 g, more preferably 0.2 g-5 g, in total. When elevation of the blood glucose level is feared such as in diabetic nephropathy, the ratio of leucine and isoleucine is preferably increased to about 1- to 2.5-fold relative to valine and histidine.

The nutrition composition of the present invention comprises, together with the above-mentioned one or more kinds selected from the group consisting of branched chain amino acid and histidine, a lipid containing ω-3 fatty acid and ω-6 fatty acid such that the weight ratio of ω-6 fatty acid to ω-3 fatty acid would be 0.5-5.5.

The "ω-3 fatty acid" is also indicated as "n-3 fatty acid", which is an unsaturated fatty acid having a double bond at the third position from the methyl group end of the hydrocarbon chain. Examples thereof include α-linolenic acid, eicosapentaenoic acid, docosapentaenoic acid, docosahexaenoic acid and the like. Since eicosapentaenoic acid is known to have an action to improve insulin resistance, it can be used more preferably for diabetic nephropathy. In the present invention, one or more kinds of these are selected and used. The "ω-6 fatty acid" is also indicated as "n-6 fatty acid", which is an unsaturated fatty acid having a double bond at the 6th position from the methyl group end of the hydrocarbon chain. Examples thereof include linoleic acid, γ-linolenic acid, stearidonic acid, arachidonic acid and the like. In the present invention, one or more kinds of these are selected and used.

The above-mentioned ω-3 fatty acid is abundantly contained in Japanese basil oil, flaxseed oil, fish oil and the like, and the ω-6 fatty acid is abundantly contained in safflower oil, sunflower oil, soybean oil, rape seed oil, evening primrose oil and the like. In the present invention, they can be extracted from these fats and oils and used after purification. It is also possible to use those produced by a chemical synthesis method, a fermentation method and the like, and a commercially available product for food can also be used. As a lipid source, moreover, fats and oils abundantly containing the aforementioned ω-3 fatty acid or ω-6 fatty acid can also be used directly.

In the present invention, ω-3 fatty acid and ω-6 fatty acid are found to be effective when the weight ratio of ω-6 fatty acid to ω-3 fatty acid is 0.5-5.5. Therefore, a lipid containing the acids in amounts meeting the aforementioned weight ratio of ω-6 fatty acid to ω-3 fatty acid is used. More preferable weight ratio is 0.5-4, which is further preferably 0.5-3, particularly preferably 0.5-2.

The required amount of lipid as recommended in Japan based on the lipid ingestion state in the past is 4 in the weight ratio of ω-6 fatty acid to ω-3 fatty acid. In the present invention, fats and oils containing ω-3 fatty acid and ω-6 fatty acid at the aforementioned weight ratio may be directly used, or a mixture of ω-3 fatty acid or fats and oils abundantly containing ω-3 fatty acid, and ω-6 fatty acid or fats and oils abundantly containing ω-6 fatty acid at the aforementioned weight ratio may also be used. The total amount of ω-3 fatty acid and ω-6 fatty acid per 100 kcal of the composition of the present invention is preferably 0.5 g-10 g.

The nutrition composition of the present invention can further contain a soybean protein or a hydrolysate thereof, in addition to one or more kinds of free amino acids selected from the group consisting of valine, leucine, isoleucine and histidine, and a lipid containing the above-mentioned ω-3 fatty acid and ω-6 fatty acid. Moreover, the nutrition composition of the present invention can also contain, a soybean protein or a hydrolysate thereof, instead of the above-mentioned lipid containing ω-3 fatty acid and ω-6 fatty acid.

As the "soybean protein", a protein separated from soybean by a conventional method can be used. Examples thereof include a product prepared by removing saccharides and the like from defatted soybean, which is obtained by removing soybean oil from whole soybean, by water extraction, separating the protein with acid and neutralizing same to give a separated soybean protein, and sterilizing and drying the protein, a product obtained by subjecting a separated soybean protein to an extruder treatment, drying and granulating the protein to give granule or fiber, low molecular weight soybean peptide obtained by reacting a separated soybean protein with an enzyme such as protease and the like. In addition, commercially available products such as "SUPRO710", "FUJIPRO", "SUNLOVER", "PRO-LEENA", "FUJINIK", "APEX", "HI-NUTE", "SOYA SOUR" (all manufactured by FUJI OIL CO., LTD.) and the like can also be used. For the object of the present invention, one having a low phosphorus concentration is preferable.

Furthermore, the protein content of the nutrition composition of the present invention is desirably not very high, and the total weight of the protein or peptide (excluding mino acids) is preferably not more than 3.5 g per 100 kcal of the composition. The protein or peptide preferably contains a soybean protein or a hydrolysate thereof in a proportion of 20 wt %-100 wt %.

In addition, the nutrition composition of the present invention can contain a medium chain fatty acid oil as a lipid source. The "medium chain fatty acid" means a fatty acid having a carbon number of 8 to 10 such as caprylic acid, capric acid and the like, and the "medium chain fatty acid oil" means fats and oils including triglyceride of the aforementioned medium chain fatty acid, and the like. The medium chain fatty acid is characterized in that it is digested and absorbed about 4 times more rapidly than long chain fatty acid generally present in fats and oils, delivered after absorption to the liver via portal vein without passing through lymphatic vessels, and rapidly metabolized. Therefore, it can be preferably utilized as an energy source.

For the object of the present invention, fats and oils containing a large amount of medium chain fatty acid such as palm oil, palm oil, palm kernel oil and the like can be used as the medium chain fatty acid oil. As the palm oil, palm oil and the like, one extracted and purified from natural plants such as palm and the like may be used. However, a commercially available product is conveniently used. In the present invention, the lipid appropriately contains 10 wt %-65 wt % of a medium chain fatty acid oil relative to the total weight the lipid.

The nutrition composition of the present invention can also contain vitamins and minerals.

Examples of the vitamins include liposoluble vitamins such as vitamin A (retinol, retinal, retinoic acid etc.); carotenoid (β-carotene etc.); vitamin D (ergocalciferol, cholecalciferol etc.); vitamin E (α-tocopherol etc.); vitamin K (phylloquinone, menaquinone etc.) and the like, and water-soluble vitamins such as vitamin $B_1$ (thiamine etc.), vitamin $B_2$ (riboflavin etc.), vitamin $B_6$ (pyridoxine, pyridoxal, pyridoxamine etc.), vitamin $B_{12}$ (cyanocobalamin etc.), niacin (nicotinic acid, nicotinic amide etc.), vitamin B group (pantothenic acid, biotin, folic acid etc.); vitamin C. As mentioned above, since addition of an antioxidant is effective for the prevention or improvement of oxidative stress associated with renal diseases, addition of vitamin C and/or vitamin E is preferable in the present invention. To afford a sufficient antioxidant action, not less than 5 mg of vitamin C and not less than 1 mg of vitamin E are preferably contained per 100 kcal of the nutrition composition of the present invention. Vitamin C is more preferably contained in not less than 15 mg. On the other hand, since occurrence of side effects due to the ingestion of a large amount of vitamin C is feared in patients with renal diseases, the amount of vitamin C is appropriately set to not more than 150 mg per 100 kcal of the composition, and moreover, the daily ingestion amount for an adult is more appropriately not more than 100 mg.

While vitamin E is not particularly limited, the daily ingestion amount for an adult is appropriately not more than 800 mg based on the amount of α-tocopherol. In addition, since vitamin A is more easily accumulated in the body of patients with renal diseases, the amount thereof to be added requires consideration, and is appropriately not more than 70 µg retinol equivalents per 100 kcal of the composition.

Examples of the minerals include conventional minerals such as sodium, potassium, magnesium, calcium, phosphorus, iodine, iron, copper, manganese, selenium, zinc, chrome, molybdenum and the like. Since the kidney function of patients with renal diseases is lower, not more than 90 mg of sodium, not more than 60 mg of potassium, and not more than 50 mg of phosphorus are preferably contained per 100 kcal of the nutrition composition of the present invention. Furthermore, mot more than 60 mg of sodium, not more than 30 mg of potassium and not more than 35 mg of phosphorus are preferably contained.

As mentioned above, since the importance of selenium and zinc in the nutrition composition for patients with renal diseases is suggested, the nutrition composition of the present invention preferably contains these in appropriate amounts. Selenium is considered to act in the body after incorporation into a protein and be mainly involved in the antioxidant function.

On the other hand, zinc is necessary for expression of the activity of enzymes involved in the immunity, wound healing, spermatogenesis, taste perception and the like. The amount thereof in the composition in consideration of the dietary intake standard for Japanese people is appropriately 2.5 µg-45 µg of selenium and 1 mg-9 mg of zinc, per 100 kcal of the composition.

The nutrition composition of the present invention desirably contains a low amount of water, which is preferably not more than 70 g per 100 kcal of the composition.

The nutrition composition of the present invention can further contain carbohydrates such as glucose, sucrose, dextrin and the like. In addition, dietary fibers such as pectin, agarose, glucomannan, cellulose, poorly soluble dextrin and the like can also be added. For ingestion by patients with renal failure derived from diabetes, a part or all of carbohydrates is preferably replaced by carbohydrates showing delayed absorption such as isomaltulose (palatinose) and the like.

Since the nutrition composition of the present invention can be daily ingested with ease, it is preferably provided in an orally ingestible form. In the present invention, one or more kinds of free amino acids selected from valine, leucine, isoleucine and histidine, a lipid containing ω-3 fatty acid and ω-6 fatty acid, and the like may be directly mixed and ingested as a nutrition composition, or the composition can also be formulated with a pharmaceutically acceptable carrier for pharmaceutical products and provided as a pharmaceutical product. Alternatively, the composition can also be provided as foods and drinks such as food with health claims such as food for specified health uses and food with nutrient function claims and the like, nutrition aid food, the other health food and the like, by adding a material for food and drink or food additive.

When the nutrition composition of the present invention is formulated and provided, it can be produced as a liquid preparation such as elixir, suspension, syrup, emulsion, ampoule and the like; a solid preparation such as gel, gum, drop, powder, granule, pill, tablet (including sugar-coated tablet, film-coated tablet), capsule, package agent, etc. and the like.

Examples of the pharmaceutically acceptable carrier for pharmaceutical products, which can be used for formulating the nutrition composition of the present invention, include cellulose and a derivative thereof such as crystalline cellulose, hydroxypropylcellulose and the like; excipients such as natural polymer compound (gum arabic, sodium alginate etc.) and the like; binders such as guar gum, stearic acid, polymeric polyvinylpyrrolidone and the like; lubricants such as talc, polyethylene glycol 6000 and the like; disintegrants such as adipic acid and the like, surfactants such as sucrose ester of fatty acid, soybean lecithin, polyoxyethylene hydrogenated castor oil, polyoxyethylene monostearic acid ester and the like; thickeners such as sodium carboxymethylcellulose, carboxyvinyl polymer, xanthan gum, gelatin and the like; coating agents such as ethyl acrylate methyl methacrylate copolymer dispersion, caramel, Carnauba wax, shellac, pullulan and the like; pH adjusters such as citric acid, sodium citrate, acetic acid, sodium acetate, sodium hydroxide and the like; antioxidants such as erythorbic acid, butylhydroxyanisole, propyl gallate and the like; flavoring agents such as aspartame, licorice extract, saccharin and the like; preservatives such as sodium benzoate, sodium edetate, sorbic acid, sodium sorbate, methyl paraoxybenzoate, butyl paraoxybenzoate and the like; colorants such as ferric oxide red, yellow iron oxide, black iron oxide, carmine, Food Color blue No. 1, Food Color yellow No. 4, Food Color Red No. 2 etc. and the like.

When the nutrition composition of the present invention can be provided as food and drink, liquid products such as drinks and the like, milk products such as milk, milk beverage, yogurt and the like, jelly products such as jelly drinks, jelly and the like, solid products such as gum product, powder product, granular product, sheet product, capsule product, tablet product, snack bar, cookie etc., and the like.

Examples of the materials for food and food additives which can be used for forming the nutrition composition of the present invention as foods and drinks include sweetener, colorant, preservative, thickening stabilizer, antioxidant, color former, bleach, fungicide, gum base, bittering agent, enzyme, gloss agent, acidulant, seasoning, emulsifier, enhancement agent, agent for production, flavor, spice and the like.

When the nutrition composition of the present invention is provided as food and drink, a package form for one ingestion amount unit can be employed. The "package form for one ingestion amount unit" is used when the amount of food and drink to be ingested per meal is determined in advance. Examples thereof include a package of an amount to be ingested at one time using a container such as pack, bag, bottle, box and the like in case of drinks, gum, jelly, yogurt, cookie and the like, and an individual package of an amount to be ingested at one time using pack, bag and the like in case of foods in the form of granule, powder, slurry and the like.

Particularly, when the foods and drinks are food with health claims such as food for specified health uses, food with nutrient function claims and the like, nutrition aid food, the other health foods and the like, a form wherein the composition of the present invention is packed in a unit amount to be ingested per meal, a form wherein the composition of the present invention is suspended or dissolved to give a drink, which is packed in a bottle etc. for a single consumption and the like can be mentioned.

The amount of the nutrition composition of the present invention to be ingested per day is individually determined depending on the age, sex, body weight, level of symptoms associated with renal diseases, level of decrease of the kidney function, meal condition and the like of patients with renal diseases, and the nutrition composition of the present invention is appropriately ingested to provide about 50 kcal-2000 kcal for an adult per day. The aforementioned amount is preferably ingested in about 1 to 3 portions a day. When the nutrition composition of the present invention is formed in a food or drink in a package form of one ingestion amount unit, the amount to be ingested one time as determined above is individually packed. Since the nutrition composition of the present invention places a small load on the kidney function, it can be ingested continuously.

Particularly, since patients with chronic renal diseases show persistent malnutrition, inflammation and the like, and have a high risk of concurrently developing arteriosclerosis, abnormal lipid metabolism and the like, the nutrition composition of the present invention is preferably ingested for a long time until the aforementioned symptoms associated with renal diseases are improved.

The nutrition composition of the present invention can be produced by conventional formulation techniques and food production techniques.

The nutrition composition of the present invention is useful as a pharmaceutical product, food and drink etc. for the prevention or improvement of malnutrition associated with renal diseases. In the patients with chronic diseases, inhibition of absorption of liposoluble vitamins, vitamin $B_{12}$, calcium and iron tends to appear due to malabsorption. Patients with renal diseases easily suffer from shortage of protein, iron and vitamin D, including patients with dialysis introduction. The shortage of protein causes protein-energy malnutrition and hypoalbuminemia. In addition, the shortage of iron causes hypoferric anemia, and the shortage of vitamin D causes osteohalisteresis and rickets.

The nutrition composition of the present invention can effectively prevent or improve the aforementioned diseases and symptoms by effectively preventing or improving such malnutrition associated with renal diseases.

The nutrition composition of the present invention is useful as a pharmaceutical product, food and drink, and the like for the prevention or improvement of inflammation associated with renal diseases. Examples of the inflammation associated with renal diseases include acute nephritis syndromes such as acute glomerulonephritis, postinfectious glomerulonephritis and the like; chronic nephritis such as chronic nephritis, slowly-progressive glomerular disease and the like; nephritic syndrome; diabetic nephropathy and the like. The nutrition composition of the present invention can effectively prevent or improve such inflammatory conditions and, for example, is particularly effective for inflammatory conditions associated with renal diseases wherein the blood CRP concentration is not less than 0.2 mg/dL, and the like.

The nutrition composition of the present invention is useful as a pharmaceutical product, food and drink, and the like for the prevention or improvement of arteriosclerosis associated with renal diseases. Examples of the arteriosclerosis associated with renal diseases include atheroarteriosclerosis due to renal failure, and the symptom is particularly problematic for patients with renal diseases who are under treatment by dialysis. The nutrition composition of the present invention can effectively prevent the onset of arteriosclerosis, and can effectively improved the symptom.

The nutrition composition of the present invention is useful as a pharmaceutical product, food and drink, and the like for the prevention or improvement of abnormal lipid metabolism associated with renal diseases. In patients with chronic renal failure, particularly patients who are under treatment by hemodialysis, the onset of abnormal lipid metabolism such as LDL cholesterolemia, hypo-high density lipoprotein cholesterolemia and hypertriglyceridemia are found. In addition, in patients with renal diseases such as nephritic syndrome and the like, the secretion of very low-density lipoprotein (VLDL) cholesterol increases, and the risk of the onset of abnormal lipid metabolism is high. As a result of the onset of abnormal lipid metabolism, the production of lipoperoxides such as LDL cholesterol peroxide and the like increases, and the risk of developing atherosclerosis becomes high.

The nutrition composition of the present invention can effectively suppress the onset of abnormal lipid metabolism such as increased blood LDL cholesterol associated with renal diseases and the like, and is useful for the prevention or improvement of abnormal lipid metabolism associated with renal diseases.

As mentioned above, since the nutrition composition of the present invention is useful for the prevention or improvement of malnutrition, inflammation, arteriosclerosis and abnormal lipid metabolism associated with renal diseases, it is effective for preventing the onset of MIA syndrome in patients with renal diseases.

For example, it is particularly effective for dialysis patients showing a blood CRP concentration of not less than 0.2 mg/dL and an albumin concentration of not more than 3.5 g/dL, and the like. Therefore, ingestion of the nutrition composition of the present invention is preferable for patients with renal diseases showing a sign of MIA syndrome such as a decreased appetite, inflammation, abnormal lipid metabolism and the like.

Active oxygen and lipoperoxide delivered by blood gather in the kidney. In renal diseases associated with inflammation, moreover, oxidative stress is enhanced more by exposure to active oxygen released by macrophage, lymphocyte and the like. Such oxidative stress causes kidney tissue disorder, oxidizes LDL cholesterol as mentioned above to produce lipoperoxide, and enhances the risk of the onset of atherosclerosis.

The nutrition composition of the present invention is useful as a pharmaceutical product, food and drink, and the like for the prevention or improvement of such oxidative stress associated with renal diseases. When the nutrition composition of the present invention contains vitamin C and vitamin E, which are antioxidants, or selenium having an antioxidant action, it shows a particularly good preventive or improving effect against oxidative stress.

In diabetic patients, moreover, diabetic nephropathy is sometimes developed due to lowered kidney function caused by thickening of renal blood vessels, injury of vascular endothelium and the like, since hyperglycemia condition persists for a long period. The nutrition composition of the present invention is also useful as a pharmaceutical product, food and drink, and the like for the prevention or improvement of such diabetic nephropathy.

Particularly, when leucine or isoleucine is used as a free amino acid, and when eicosapentaenoic acid is used as a ω-3 fatty acid, the composition can be preferably used, since a suppressive action on postprandial elevation of blood glucose levels and insulin resistance-improving effect are found.

Therefore, in other embodiment of the present invention, an agent for the prevention or improvement of one or more symptoms selected from the group consisting of malnutrition, inflammation, arteriosclerosis, abnormal lipid metabolism and oxidative stress associated with renal disease, or an agent for the prevention or improvement of diabetic nephropathy can be obtained by adding one or more kinds of free amino acids selected from the group consisting of valine, leucine, isoleucine and histidine, and a lipid containing ω-3 fatty acid and ω-6 fatty acid such that the weight ratio of ω-6 fatty acid to ω-3 fatty acid is 0.5-5.5. The aforementioned preventive or improving agent can further contain a soybean protein or a hydrolysate thereof.

In addition, the present invention can provide an agent for the prevention or improvement of one or more symptoms selected from the group consisting of malnutrition, inflammation, arteriosclerosis, abnormal lipid metabolism and oxidative stress associated with renal disease, or an agent for the prevention or improvement of diabetic nephropathy, by adding one or more kinds of free amino acids selected from the group consisting of valine, leucine, isoleucine and histidine, and a soybean protein or a hydrolysate thereof.

The above-mentioned agent for the prevention or improvement of various symptoms associated with renal diseases, or the agent for the prevention or improvement of diabetic nephropathy can contain the aforementioned medium chain fatty acid oil, vitamins (preferably vitamin C and/or vitamin E), minerals (preferably selenium and zinc), carbohydrate, dietary fiber and the like.

In addition, the present invention provides a method for the prevention or improvement of one or more symptoms selected from the group consisting of malnutrition, inflammation, arteriosclerosis, abnormal lipid metabolism and oxidative stress associated with renal disease, comprising administering, to patients with renal diseases, each of the above-mentioned nutrition compositions in an amount sufficient for the prevention or improvement of the above-mentioned one or more symptoms, and a method for the prevention or improvement of diabetic nephropathy, comprising administering, to patients with diabetic nephropathy, an amount sufficient for the prevention or improvement of diabetic nephropathy.

While the amount sufficient for the prevention or improvement of the above-mentioned one or more symptoms selected from the group consisting of malnutrition, inflammation, arteriosclerosis, abnormal lipid metabolism and oxidative stress associated with renal disease, and the amount sufficient for the prevention or improvement of diabetic nephropathy vary depending on the age, sex, body weight, level of symptoms associated with renal diseases or level of diabetic nephropathy, degree of decrease of the kidney function, meal condition of the patient and the like, the nutrition composition of the present invention is ingested to provide about 50 kcal-2000 kcal for an adult per day.

Furthermore, in another embodiment of the present invention, a commercial package can be provided, which contains each of the above-mentioned nutrition compositions, and a document describing that the nutrition composition can or should be used for the prevention or improvement of one or more symptoms selected from the group consisting of malnutrition, inflammation, arteriosclerosis, abnormal lipid metabolism and oxidative stress associated with renal disease, and a commercial package containing each of the above-mentioned nutrition compositions, and a document describing that the nutrition composition can or should be used for the prevention or improvement of diabetic nephropathy.

EXAMPLES

The present invention is explained in detail in the following by referring to Examples.

Example 1

Jelly Drink for Patients with Renal Diseases

In consideration of optimal nutrition effect for patients with renal diseases, the nutrient composition shown in Table 1 was formed, and based thereon, a jelly drink was prepared as the nutrition composition of the present invention. That is, to give the composition in Table 1, each component and a polysaccharide thickener were added to water, and the mixture was mixed, stirred, emulsified and adjusted to pH 3.8 after cooling. Furthermore, the composition was sterilized by heating at 80° C. for 10 min, cooled and filled in a pouch.

TABLE 1

| ingredients | contained amount/100 kcal | calorie % |
|---|---|---|
| nitrogen source | 2.50 g | 10 |
| L-valine | 0.29 g | |
| L-leucine | 0.48 g | |
| L-isoleucine | 0.24 g | |
| soybean protein | 1.50 g | |
| lipid | 3.35 g | 30 |
| rape seed oil | 1.29 g | |
| medium chain fatty acid oil | 1.40 g | |
| eicosapentaenoic acid | 0.66 g | |
| ω-6/ω-3 ratio | 0.77 | |
| medium chain fatty acid ratio | 42 | |
| carbohydrate dextrin + sucrose | 15.0 g | 60 |
| sodium | <60 mg | |
| potassium | <30 mg | |
| magnesium | 26 mg | |
| calcium | <5 mg | |
| phosphorus | <35 mg | |
| iodine | 13 μg | |
| iron | 1.2 mg | |
| copper | 0.12 mg | |
| manganese | 0.34 mg | |
| selenium | 9 μg | |
| zinc | 1.8 mg | |
| chromium | 2.5 μg | |
| molybdenum | 2.1 μg | |
| vitamin A | 22.5 μg RE*1 | |
| retinol | 15 μg | |
| β-carotene | 90 μg | |
| vitamin D | 0.1 μg | |
| vitamin E | 2.75 mg α-TE*2 | |
| vitamin K | 6.3 μg | |
| vitamin B$_1$ | 0.6 mg | |
| vitamin B$_2$ | 0.36 mg | |
| vitamin B$_6$ | 0.6 mg | |
| vitamin B$_{12}$ | 0.5 μg | |
| niacin | 2.4 mg NE*3 | |
| pantothenic acid | 0.5 mg | |
| biotin | 4.5 μg | |
| folic acid | 60 μg | |
| vitamin C | 15 mg | |

*1 retinol equivalent
*2 based on α-tocopherol
*3 niacin equivalent

Example 2

Milk Beverage for Patients with Renal Diseases Associated with Diabetes

In consideration of the optimal nutrition effect for patients with renal diseases associated with diabetes, the nutrient composition shown in Table 2 was formed, based on which a milk beverage was prepared as the nutrition composition of the present invention. That is, each component and an emulsifier were added to water to give the composition of Table 2, mixed, and an emulsion step was repeatedly performed plural times in a high-pressure emulsifying machine under pressurization of 500-1,000 kg/cm² to give an emulsion composition. The emulsion composition was filled in an aluminum bag by a conventional filling machine, and sterilized by a retort sterilization machine under general conditions. The milk beverage of this Example stably contained all ingredients one year later, and the viscosity at 25° C. was 9 mPa·s.

TABLE 2

| ingredients | contained amount/100 kcal | calorie % |
|---|---|---|
| nitrogen source | 2.50 g | 10 |
| L-valine | 0.29 g | |
| L-leucine | 0.48 g | |
| L-isoleucine | 0.24 g | |
| L-histidine | 0.30 g | |
| soybean protein | 1.20 g | |
| lipid | 3.35 g | 30 |
| rape seed oil | 1.01 g | |
| medium chain fatty acid oil | 1.40 g | |
| eicosapentaenoic acid | 0.94 g | |
| ω-6/ω-3 ratio | 0.50 | |
| medium chain fatty acid ratio | 42 | |
| carbohydrate dextrin + palatinose | 15.0 g | 60 |
| Sodium | <60 mg | |
| potassium | <30 mg | |
| magnesium | 26 mg | |
| calcium | <5 mg | |
| phosphorus | <35 mg | |
| iodine | 13 μg | |
| iron | 1.2 mg | |
| copper | 0.12 mg | |
| manganese | 0.34 mg | |
| selenium | 9 μg | |
| zinc | 1.8 mg | |
| chromium | 2.5 μg | |
| molybdenum | 2.1 μg | |
| vitamin A | 22.5 μg RE*1 | |
| retinol | 15 μg | |
| β-carotene | 90 μg | |
| vitamin D | 0.1 μg | |
| vitamin E | 2.75 mg α-TE*2 | |
| vitamin K | 6.3 μg | |
| vitamin B$_1$ | 0.6 mg | |
| vitamin B$_2$ | 0.36 mg | |
| vitamin B$_6$ | 0.6 mg | |
| vitamin B$_{12}$ | 0.5 μg | |
| niacin | 2.4 mg NE*3 | |
| pantothenic acid | 0.5 mg | |
| biotin | 4.5 μg | |
| folic acid | 60 μg | |
| vitamin C | 15 mg | |

*1 retinol equivalent
*2 based on α-tocopherol
*3 niacin equivalent

Example 3

Acidic Drinks for Patients with Renal Diseases in Need of Protein-Intake Restriction In consideration of the optimal nutrition effect for patients with renal diseases in need of protein-intake restriction, the nutrient composition shown in Table 3 was formed, based on which an acidic drink was prepared as the nutrition composition of the present invention. That is, each component was added to water to give the composition of Table 3, mixed and stirred and adjusted to pH 3.8. Furthermore, the mixture was sterilized by heating at 80° C. for 10 min, cooled and filled in a bottle.

TABLE 3

| ingredients | contained amount/100 kcal | calorie % |
|---|---|---|
| nitrogen source | 1.50 g | 6 |
| L-valine | 0.29 g | |
| L-leucine | 0.48 g | |
| L-isoleucine | 0.24 g | |
| soybean protein | 1.50 g | |
| lipid | 3.56 g | 32 |
| rape seed oil | 2.95 g | |
| medium chain fatty acid oil | 0.36 g | |
| eicosapentaenoic acid | 0.25 g | |
| ω-6/ω-3 ratio | 5.50 | |
| medium chain fatty acid ratio | 10 | |
| carbohydrate dextrin + sucrose | 15.5 g | 62 |
| sodium | <60 mg | |
| potassium | <30 mg | |
| magnesium | 26 mg | |
| calcium | <5 mg | |
| phosphorus | <35 mg | |
| iodine | 13 μg | |
| iron | 1.2 mg | |
| copper | 0.12 mg | |
| manganese | 0.34 mg | |
| selenium | 9 μg | |
| zinc | 1.8 mg | |
| chromium | 2.5 μg | |
| molybdenum | 2.1 μg | |
| vitamin A | 22.5 μg RE*[1] | |
| retinol | 15 μg | |
| β-carotene | 90 μg | |
| vitamin D | 0.1 μg | |
| vitamin E | 2.75 mg α-TE*[2] | |
| vitamin K | 6.3 μg | |
| vitamin $B_1$ | 0.6 mg | |
| vitamin $B_2$ | 0.36 mg | |
| vitamin $B_6$ | 0.6 mg | |
| vitamin $B_{12}$ | 0.5 μg | |
| niacin | 2.4 mg NE*[3] | |
| pantothenic acid | 0.5 mg | |
| biotin | 4.5 μg | |
| folic acid | 60 μg | |
| vitamin C | 15 mg | |

*[1]retinol equivalent
*[2]based on α-tocopherol
*[3]niacin equivalent

Example 4

Concentrated Composition for Patients with Renal Diseases

In the same manner as in the above-mentioned Example 1 except that vitamins, minerals, carbohydrates and medium chain fatty acid were removed, the composition was obtained. The composition of this Example is useful as a dietary supplement, and can show a superior effect even by adding to a general liquid food.

Experimental Example 1

Consideration of Optimal Content Weight Ratio of ω-6 Fatty Acid to ω-3 Fatty Acid in Inflammation Derived from Arteriosclerosis Regarding the unsaturated fatty acid to be used as a lipid source in the nutrition composition of the present invention, an influence of the content weight ratio of ω-6 fatty acid to ω-3 fatty acid on the effect of prevention or improvement of malnutrition, inflammation and the like was studied by the following experiment. That is, 6-week-old male SD rats were divided into 4 groups (each group n=6), and each fed with an equal amount of a feed containing a lipid having the composition shown in Table 4, and materials other than lipid according to the standard purification feed AIN93G (manufactured by CLEA Japan, Inc.) for 2 weeks. Thereafter, the blood was drawn from the jugular vein, and CRP concentration and LDL cholesterol concentration in the plasma were quantified by a conventional method. The test results are shown in Table 5.

TABLE 4

| animal group | lipid composition | ω-6 fatty acid/ω-3 fatty acid (weight ratio) |
|---|---|---|
| 1A | soybean oil alone (control) | 7.9 |
| 1B | CCT + soybean oil:safflower oil (9:5) | 14.0 |
| 1C | CCT + soybean oil | 7.9 |
| 1D | CCT + soybean oil:fish oil (9:5) (eicosapentaenoic acid content = 186 mg/100 kcal) | 1.6 |

TABLE 5

| animal group | Body weight gain (g) | CRP (μg/mL) | LDL cholesterol (mg/dL) |
|---|---|---|---|
| 1A | 39.6 ± 8.0 | 287 ± 23 (100) | 9 ± 2 |
| 1B | 18.0 ± 9.9 | 352 ± 21 (123) | 593 ± 124 |
| 1C | 19.4 ± 6.2 | 391 ± 122 (136) | 495 ± 162 |
| 1D | 26.9 ± 7.3 | 289 ± 62 (101) | 206 ± 48 |

The "CCT" in Table 4 means 4 wt % cholesterol, 1 wt % cholic acid and 0.5 wt % thiouracil, and has an action to induce inflammation of blood vessel similar to arteriosclerosis. In Table 5, 3 groups of 1B, 1C and 1D ingested with CCT-containing feed showed a less increase in the body weight as compared to control (1A) group; however, group 1D showed a greater increase in the body weight as compared to group 1B and group 1C. CRP to be the index of inflammation increased to 123% and 136% in group 1B ingested with a feed containing CCT and a lipid wherein the content weight ratio of ω-6 fatty acid to ω-3 fatty acid was 14.0, and group 1C ingested with a feed containing CCT and a lipid wherein the weight ratio of the aforementioned fatty acids is 7.9, respectively, based on the value of control (1A) group as 100%. In contrast, in group 1D ingested with a feed containing a lipid wherein the content weight ratio of ω-6 fatty acid to ω-3 fatty acid is 1.6, such an increase in CRP was suppressed to the level same as the value of control group 1A.

In addition, as for the LDL cholesterol value to be the index of abnormal lipid metabolism such as hyperlipidemia, group 1B and group 1C showed a remarkable increase; however, group 1D showed an increase to about half of that of group 1B and group 1C. As for the LDL cholesterol value, a significant difference was found between groups 1D and 1B, and groups 1D and 1C (p<0.05).

From the results of the above-mentioned experiments, it was found that a nutrition condition-improving effect, an inflammation suppressive effect and an abnormal lipid metabolism-improving effect were obtained by reducing the content weight ratio of ω-6 fatty acid to ω-3 fatty acid to less than 7.9, and further reducing to around 1.6.

When a similar test was performed using lipids wherein the content weight ratios of ω-6 fatty acid to ω-3 fatty acid were 0.5, 2.0, 3.0 and 5.5, similarly good nutrition condition-improving effect, inflammation suppressive effect and abnormal lipid metabolism-improving effect were found.

Experimental Example 2

Consideration of Influence of Free Amino Acid in Inflammation Derived from Inflammatory Cytokine Dialysis patients are known to show a higher blood level of interleukin (IL)-6, which is an inflammatory cytokine, than healthy individual. Therefore, the following experiment was performed to study an influence of free amino acid to be used in the present invention on inflammation derived from IL-6. That is, an osmotic pump (flow rate 240 μL/day) was subcutaneously embedded in the lumbar middle portion of the back of 6-week-old male SD rats, and they were divided into 3 groups (each group n=5). In the osmotic pump of group 2A was filled 1 wt % inactivated serum containing phosphate buffered saline (PBS) (solvent), and in the osmotic pumps of group 2B and group 2C was filled IL-6 such that the final dose was 400 μg/day/kg rat. In addition, as shown in Table 6, group 2A and group 2B were freely ingested with a feed obtained by adding a 5 wt % soybean protein to protein-free standard purification feed AIN93G (manufactured by CLEA Japan, Inc.), and group 2C was freely ingested with a feed obtained by further adding 0.5 wt % (0.13 g/100 kcal) free amino acid (valine:leucine:isoleucine=1.2:2:1) both for 1 week.

The feed given to each group was amended with cornstarch to reach the equal ingestion calorie for each group. Thereafter, the blood was drawn from the abdominal aorta under anesthesia, and the plasma CRP concentration was quantified by a conventional method. The results are shown in Table 7.

TABLE 6

| animal group | administered substance | feed composition |
|---|---|---|
| 2A | solvent | standard purification feed + 5 wt % soybean protein |
| 2B | IL-6 | standard purification feed + 5 wt % soybean protein |
| 2C | IL-6 | standard purification feed + 5 wt % soybean protein + 0.5 wt % branched chain amino acid |

TABLE 7

| animal group | CRP concentration (μg/mL) |
|---|---|
| 2A | 113 ± 62.6 |
| 2B | 559 ± 88.8 |
| 2C | 490 ± 49.2 |

In group 2B administered with IL-6, CRP, which is an index of inflammation, increased to nearly 5 times that of control group 2A. However, group 2C administered with free amino acid showed 12.4% suppression as compared to group 2B. It was suggested that an effective prophylactic or improving effect on inflammation can be expected even when inflammatory cytokine is loaded from the outside on patients with renal diseases. That is, this experiment showed usefulness of the combined use of free amino acid such as branched chain amino acid and the like, and a soybean protein.

Experimental Example 3

Consideration of Influence of Content Weight Ratio of ω-6 Fatty Acid to ω-3 Fatty Acid and Free Amino Acid and Soybean Protein Used in the Present Invention on Inflammation Derived from Arteriosclerosis Associated with Renal Diseases Then, regarding the unsaturated fatty acid used as a lipid source in the nutrition composition of the present invention, an influence of the content weight ratio of ω-6 fatty acid to ω-3 fatty acid, and free amino acid and soybean protein used in the present invention on each index value of inflammation associated with renal diseases was considered. In this experiment, 6-week-old male SD rats underwent a sham surgery or an operation to remove ⅚ of the kidney and, after a recovery period of 1 week, they were divided into 3 groups (each group n=7) shown in Table 8. As a rat normal feed for group 3A, a feed obtained by removing protein from standard purification feed AIN93G (manufactured by CLEA Japan, Inc.), adding only milk protein to achieve a protein content of 2.5 wt %, and amending the feed with cornstarch to a calorie equal to that of AIN93G having a protein content of 20 wt % was used. As a commercially available nutrition product R for patients with renal diseases which was given to group 3B, a feed obtained by mixing feeds having a protein content of 3.5 g and 1.0 g per 100 kcal at 2:3 to achieve a protein content of 2.5 g per 100 kcal, and freeze-drying the mixture was used. Nutrition product R does not contain, as shown in Table 9, a soybean protein, free branched chain amino acid and the like, and the content weight ratio of ω-6 fatty acid to ω-3 fatty acid is 3.4. As the feed for group 3C, nutrition composition A of the present invention as shown in Table 9 was used. The feeds for groups 3B and 3C contained the above-mentioned CCT (cholesterol:cholic acid:thiouracil=8:2:1, 1.46 g) per 100 kcal of the test feed.

After rearing each group on the equal amount of the aforementioned feed for 2 weeks, the blood was drawn from the jugular vein, and CRP (inflammatory index), IL-6 and leukocyte count, neutrophil count, which are peripheral blood items, and albumin/globulin (A/G) ratio (index of serum protein and the like) in the plasma were quantified by conventional methods. The results are shown in Table 10.

TABLE 8

| animal group | operation | feed content |
|---|---|---|
| 3A | sham surgery | general feed for rats |
| 3B | 5/6 kidney removal | nutrition product R added with CCT |
| 3C | 5/6 kidney removal | nutrition composition A of the present invention added with CCT |

TABLE 9

| | content/100 kcal | |
|---|---|---|
| ingredient | nutrition product R | nutrition composition A of the present invention |
| protein (g) | 2.5 | 2.5 |
| milk protein (g) | 2.5 | — |
| soybean protein (g) | — | 1.5 |
| L-valine (g) | — | 0.29 |
| L-leucine (g) | — | 0.48 |
| L-isoleucine (g) | — | 0.24 |
| fat (g) | 2.8 | 3.35 |
| ω-6 fatty acid/ω-3 fatty acid (weight ratio) | 3.4 | 0.77 |
| carbohydrate (g) | 15.9 | 15 |

TABLE 10

| | animal group | | |
|---|---|---|---|
| quantified item | 3A | 3B | 3C |
| CRP (μg/mL) | 99 ± 18 | 489 ± 198.95 | 256 ± 101 |
| IL-6 (pg/mL) | 4 ± 4 | 54 ± 76 | 18 ± 19 |
| leukocyte count ($10^2$/μL) | 92 ± 37 | 139 ± 37 | 120.97 ± 42 |
| neutrophil count ($10^2$/μL) | 12 ± 7 | 62 ± 19 | 36 ± 17 |
| A/G ratio | 0.91 ± 0.08 | 0.68 ± 0.13 | 0.78 ± 0.1496 |

In Table 10, when CCT was added to the general feed in addition to nephrectomy, group 3B ingested with a commercially available nutrition product R for patients with renal diseases showed a remarkable increase in CRP (inflammation index), IL-6 (inflammatory cytokine), leukocyte count and neutrophil count. However, group 3C ingested with the nutrition composition A of the present invention showed suppression of such increase in the values of all items. Particularly, the decreased amount of CRP was as high as 233 μg/mL, and an effect exceeding the added effect of the decreased amount (102 μg/mL) of CRP found by changing the content weight ratio of ω-6 fatty acid to ω-3 fatty acid from 7.9 to 1.6 in Experimental Example 1, and the decreased amount (69 μg/mL) of CRP found by adding free branched chain amino acid to the soybean protein in Experimental Example 2 was considered to have been obtained. In addition, as for A/G ratio, which is one of the indices of nutrition condition, group 3B showed a significant decrease as compared to the sham surgery group (group 3A) free of ingestion of CCT ($p<0.05$), whereas group 3C showed suppression of such decrease. This experiment have suggested that the content weight ratio of ω-6 fatty acid to ω-3 fatty acid, and the addition of free amino acid and soybean protein used in the present invention exert an important influence on the prevention or improvement of inflammation in patients with renal diseases associated with inflammation.

INDUSTRIAL APPLICABILITY

As mentioned above in detail, the present invention can effectively prevent or improve malnutrition, inflammation, arteriosclerosis, abnormal lipid metabolism, oxidative stress, and the like, associated with renal diseases in patients with renal diseases, and also provides a nutrition composition useful for the prevention or improvement of diabetic nephropathy. Furthermore, the present invention provides a nutrition composition which is high safe and can be continuously used as a food for nutrition supplementation for patients with renal diseases, who show decreased kidney function.

The present invention is based on JP 2008-310955 filed in Japan, the contents of which are encompassed in full herein.

The invention claimed is:

1. A method for preventing or improving at least one symptom selected from the group consisting of malnutrition, inflammation, arteriosclerosis, abnormal lipid metabolism and oxidative stress, associated with renal disease, comprising:
   administering, to a subject in need thereof, 50 kcal to 2000 kcal of a nutrition composition for an adult per day,
   wherein the nutrition composition comprises at least one free amino acid selected from the group consisting of valine, leucine, isoleucine, and histidine, a lipid comprising at least one ω-3 fatty acid and at least one ω-6 fatty acid in a weight ratio of ω-6 fatty acid to ω-3 fatty acid of 0.5 to 5.5, a carbohydrate, and a soybean protein or a hydrolysate thereof,
   in the nutrition composition, the total amount of protein and peptide is not more than 3.5 g per 100 kcal of the nutrition composition, the soybean protein or a hydrolysate thereof comprises 20 wt % to 100 wt % of any proteins or peptides present, a content of the protein and peptide is 6 calorie % to 10 calorie %, a content of the lipid is 30 calorie % to 32 calorie %, and a content of the carbohydrate is 60 calorie % to 62 calorie %, and
   the subject in need thereof is a patient having at least one symptom selected from the group consisting of malnutrition, inflammation, arteriosclerosis, abnormal lipid metabolism and oxidative stress, associated with renal disease.

2. A method according to claim 1, wherein the nutrition composition further comprises 5 mg to 150 mg of vitamin C, per 100 kcal of the composition.

3. A method according to claim 1, wherein the nutrition composition comprises the at least one free amino acid in an amount of 0.1 g to 10 g per 100 kcal of the composition.

4. A method according to claim 1, wherein the ω-3 fatty acid is at least one fatty acid selected from the group consisting of α-linolenic acid, eicosapentaenoic acid, docosapentaenoic acid, and docosahexaenoic acid.

5. A method according to claim 1, wherein the ω-6 fatty acid is at least one fatty acid selected from the group consisting of linoleic acid, γ-linolenic acid, stearidonic acid, and arachidonic acid.

6. A method according to claim 1, wherein the lipid comprises 10 wt % to 65 wt % of medium chain fatty acid oil.

7. A method according to claim 1, wherein the nutrition composition further comprises not less than 1 mg of vitamin E, per 100 kcal of the nutrition composition.

8. A method according to claim 1, wherein the nutrition composition further comprises 5 mg to 150 mg of vitamin C and not less than 1 mg of vitamin E, per 100 kcal of the nutrition composition.

9. A method according to claim 1, wherein the nutrition composition further comprises 2.5 µg to 45 µg of selenium and 1 mg to 9 mg of zinc, per 100 kcal of the nutrition composition.

10. A method according to claim 1, wherein the subject in need thereof is a patient having at least one symptom selected from the group consisting of inflammation, arteriosclerosis, abnormal lipid metabolism and oxidative stress, associated with renal disease, and the nutrition composition is administered to the subject in an amount sufficient to improve the one or more symptoms.

11. A method according to claim 10, wherein the subject in need thereof is a patient under a dialysis treatment.

12. A method according to claim 10, wherein the subject is a human adult.

13. A method for preventing or improving diabetic nephropathy, comprising:
   administering, to a subject in need thereof, 50 kcal to 2000 kcal of a nutrition composition for an adult per day,
   wherein the nutrition composition comprises at least one free amino acid selected from the group consisting of valine, leucine, isoleucine, and histidine, a lipid comprising at least one ω-3 fatty acid and at least one ω-6 fatty acid in a weight ratio of ω-6 fatty acid to ω-3 fatty acid of 0.5 to 5.5, a carbohydrate, and a soybean protein or a hydrolysate thereof,
   in the nutrition composition, the total amount of protein and peptide is not more than 3.5 g per 100 kcal of the nutrition composition, the soybean protein or a hydrolysate thereof comprises 20 wt % to 100 wt % of any proteins or peptides present, a content of the protein and peptide is 6 calorie % to 10 calorie %, a content of the lipid is 30 calorie % to 32 calorie %, and a content of the carbohydrate is 60 calorie % to 62 calorie %, and the subject in need thereof is a patient with diabetic nephropathy.

14. A method according to claim 13, wherein the nutrition composition comprises the at least one free amino acid in an amount of 0.1 g to 10 g per 100 kcal of the nutrition composition.

15. A method according to claim 13, wherein the ω-3 fatty acid is at least one fatty acid selected from the group consisting of α-linolenic acid, eicosapentaenoic acid, docosapentaenoic acid, and docosahexaenoic acid.

16. A method according to claim 13, wherein the ω-6 fatty acid is at least one fatty acid selected from the group consisting of linoleic acid, γ-linolenic acid, stearidonic acid, and arachidonic acid.

17. A method according to claim 13, wherein the lipid comprises 10 wt % to 65 wt % of medium chain fatty acid oil.

18. A method according to claim 13, wherein the nutrition composition further comprises not less than 1 mg of vitamin E, per 100 kcal of the nutrition composition.

19. A method according to claim 13, wherein the nutrition composition further comprises 5 mg to 150 mg of vitamin C and not less than 1 mg of vitamin E, per 100 kcal of the nutrition composition.

20. A method according to claim 13, wherein the nutrition composition further comprises 2.5 µg to 45 µg of selenium and 1 mg to 9 mg of zinc, per 100 kcal of the nutrition composition.

21. A method according to claim 13, wherein the nutrition composition further comprises 5 mg to 150 mg of vitamin C, per 100 kcal of the nutrition composition.

* * * * *